US008076318B2

(12) United States Patent
Lawrence et al.

(10) Patent No.: US 8,076,318 B2
(45) Date of Patent: Dec. 13, 2011

(54) CAGED LIGANDS AND USES THEREOF

(75) Inventors: David S. Lawrence, Hartsdale, NY (US); Richard G. Pestell, Great Falls, VA (US); Christopher Albanese, Pelham Manor, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1550 days.

(21) Appl. No.: 10/532,009

(22) PCT Filed: Oct. 22, 2003

(86) PCT No.: PCT/US03/33438
§ 371 (c)(1),
(2), (4) Date: Nov. 16, 2005

(87) PCT Pub. No.: WO2004/037983
PCT Pub. Date: May 6, 2004

(65) Prior Publication Data
US 2006/0240088 A1    Oct. 26, 2006

Related U.S. Application Data

(60) Provisional application No. 60/420,898, filed on Oct. 24, 2002.

(51) Int. Cl.
*A61K 31/56* (2006.01)
*A01N 45/00* (2006.01)
(52) U.S. Cl. .................... 514/171; 424/198.1
(58) Field of Classification Search .................... 514/171
See application file for complete search history.

(56) References Cited

U.S. PATENT DOCUMENTS

| | | | |
|---|---|---|---|
| 5,399,346 A | 3/1995 | Anderson et al. | |
| 5,635,608 A | 6/1997 | Haugland et al. | |
| 6,242,188 B1 | 6/2001 | Dattagupta et al. | |
| 6,258,603 B1 | 7/2001 | Carlson et al. | |
| 6,514,722 B2 | 2/2003 | Palsson et al. | |
| 6,803,479 B2 * | 10/2004 | Kao et al. | 560/21 |
| 2002/0152493 A1 | 10/2002 | Allen | |
| 2004/0023203 A1 | 2/2004 | Miesenbock et al. | |
| 2004/0166553 A1 | 8/2004 | Nguyen et al. | |
| 2005/0051706 A1 | 3/2005 | Witney et al. | |
| 2005/0054024 A1 | 3/2005 | Lawrence | |
| 2005/0059028 A1 | 3/2005 | Nguyen et al. | |
| 2005/0282203 A1 | 12/2005 | Nguyen et al. | |
| 2006/0211075 A1 | 9/2006 | Lawrence et al. | |
| 2007/0254312 A1 | 11/2007 | Lawrence | |
| 2008/0318246 A1 | 12/2008 | Lawrence et al. | |
| 2009/0035796 A1 | 2/2009 | Lawrence et al. | |

FOREIGN PATENT DOCUMENTS

| | | |
|---|---|---|
| WO | WO 2004/018686 A1 | 3/2004 |
| WO | WO 2008/070152 A2 | 6/2008 |
| WO | WO 2008/085260 A2 | 7/2008 |

OTHER PUBLICATIONS

Lawrence D S et al., entitled "The preparation and in vivo applications of caged peptides and proteins," Current Opinion in Chemical Biology 2005, 9:570-575.
Chen C A et al., entitled "Design and synthesis of a fluorescent reporter of protein kinase activity," J Am Chem Soc., Apr. 17, 2002;124(15):3840-1.
Yeh R H et al., "Real Time Visualization of Protein Kinase Activity in Living Cells," The Journal of Biological Chemistry, 277(13): 11527-11532, 2002.
Sharma V et al., entitled "Peptide-based Fluorescent Sensors of Protein Kinase Activity: Design and Applications," Biochim Biophys Acta., Jan. 2008; 1784(1):94-99.
Sharma et al., entitled "Deep Quench: An Expanded Dynamic Range for Protein Kinase Sensors," J Am Chem Soc., Mar. 14, 2007; 129(10):2742-2743.
PCT International Preliminary Examination Report received from the U.S. Patent Trademark Office in connection with PCT International Patent Application No. PCT/US2003/33438, 3 pages.
Adams, S.R. and Tsien, R.Y. (1993) "Controlling Cell Chemistry with Caged Compounds." Annu. Rev. Physiol. vol. 55. pp. 755-784.
Albanese, C. et al. (2002) "Recent advances in inducible expression in transgenic mice." Sem. in Cell & Develop. Biol. vol. 13. pp. 129-141.
Albanese, C. et al. (2000) "Sustained mammary gland-directed, ponasterone A-inducible expression in transgenic mice." FASEB J. vol. 14, pp. 877-884.
Ando, H. et al. (2001) "Photo-mediated gene activation using caged RNA/DNA in zebrafish embryos." Nature Genetics. vol. 28. pp. 317-325. Arakawa, H. et al. (2001) "Mutant loxP vectors for selectable marker recycle and conditional knock-outs." BMC Biotechnol. vol. 1, No. 7. pp. 1472-1479.
Belshaw, P.J. et al. (1996) "Controlling programmed cell death with a cyclophilin-cyclosporin-based chemical inducer of dimerization." Chem. Biol. vol. 3, No. 9. pp. 731-738.
Chen, J.D. and Evans, R.M. (1995) "A transcriptional co-repressor that interacts with nuclear hormone receptors." Nature vol. 377, pp. 454-457.
Cronin, C.A. et al. (2001) "The lac operator-repressor system is functional in the mouse." Genes Dev. vol. 15. pp. 1506-1517.
Cruz, F.G. et al. (2000) "Light-Activated Gene Expression." J. Am. Chem. Soc. vol. 122. pp. 8777-8778.
Curley, K. and Lawrence, D.S. (1999) "Light-activated proteins." Cur. Opin. Chem. Biol. vol. 3. pp. 84-88.
Dinan, L. et al. (1999) "An extensive ecdysteroid CoMFA." J. Comput. Aided Mol. Des. vol. 13. pp. 185-207.

(Continued)

*Primary Examiner* — Jake M. Vu
(74) *Attorney, Agent, or Firm* — Amster, Rothstein & Ebenstein LLP

(57) ABSTRACT

Provided are caged compounds comprising a ligand that specifically reacts with a receptor not naturally present in mammals. The cage is released from the ligand upon illumination of the compound with light. Also provided are cells transfected with a gene of interest and a gene encoding a receptor, the gene of interest operably linked to a genetic element capable of being induced by the receptor when bound to a ligand, and the receptor not naturally present in the species of the cell. The cells also comprise a caged ligand of the receptor. Additionally provided are methods of inducing a gene of interest in the above cells. Also provided are methods of repressing a gene of interest in a cell using caged ligands of receptors. Methods are additionally provided for inducing elimination of a target sequence in a cell of a species, using a caged ligand and a recombinase.

9 Claims, 5 Drawing Sheets

OTHER PUBLICATIONS

Feil, R. et al. (1996) "Ligand-activated site-specific recombinaton in mice." Proc. Natl. Acad. Sci. USA. vol. 93. pp. 10887-10890.

Fisher, G.H. et al. (1999) "Development of a flexible and specific gene delivery system for production of murine tumor models." Oncogene. vol. 18. pp. 5253-5260.

Furuta, T. et al. (1999) "Brominated 7-hydroxycoumarin-4-ylmethyls: Photolabile protecting groups with biologically useful cross-sections for two photon photolysis." Proc. Natl. Acad. Sci. USA. vol. 96. pp. 1193-1200.

Gingrich, J.R. and Roder, J. (1998) "Inducible Gene Expression in the Nervous System of Transgenic Mice." Annu. Rev. Neurosci. vol. 21. pp. 377-405.

Mikitani, K. (1996) "A New Nonsteroidal Chemical Class of Ligand for the Ecdysteroid Receptor 3, 5-di-tert-butyl-4-hydroxy-N-isobutyl-benzamide Shows Apparent Insect Molting Hormone Activities at Molecular and Cellular Levels." Biochem. Biophys. Res. Comm. vol. 227. pp. 427-432.

Monroe, W.T. et al. (1999) "Targeting Expression with Light Using Caged DNA." J. Biol. Chem. vol. 274. No. 30. pp. 20895-20900.

Nagy, A. (2000) "Cre Recombinase: The Universal Reagent for Genome Tailoring." Genesis. vol. 26, pp. 99-109.

No, D. et al. (1996) "Ecdysone-inducible gene expression in mammalian cells and transgenic mice." Proc Natl Acad Sci USA. vol. 93. pp. 3346-3351.

Orsulic, S. et al. (2002) "Induction of ovarian cancer by defined multiple genetic changes in a mouse model system." Cancer Cell. vol. 1. pp. 53-62.

Pao, E. et al. (2003) "Use of avian retroviral vectors to introduce transcriptional regulators into mammalian cells for analyses of tumor maintenance." Proc. Natl. Acad. Sci. USA. vol. 100. No. 15. pp. 8764-8769.

Petit, D.L. et al. (1997) "Chemical Two-Photon Uncaging: a Novel Approach to Mapping Glutamate Receptors." Neuron. vol. 19. pp. 465-471.

Ryding, A.D.S. et al. (2001) "Conditional transgenic technologies." J. Endocrinol. vol. 171. pp. 1-14.

Saez, E. et al. (2000) "Identification of ligands and coligands for the ecdysone-regulated gene switch." Proc. Natl. Acad. Sci. USA. vol. 97. No. 26. pp. 14512-14517.

Shockett, P.E. and Schatz, D.G. (1996) "Diverse strategies for tetracycline-regulated inducible gene expression." Proc. Natl. Acad. Sci. USA. vol. 93. pp. 5173-5176.

Wang, J. et al. (1998) "ETO, fusion partner in t(8;21) acute myeloid leukemia, represses transcription by interaction with the human N-CoR/mSin3/HDAC1 complex." Proc. Natl. Acad. Sci. USA. vol. 95. pp. 10860-10865.

* cited by examiner

CAGED LIGANDS AND USES THEREOF

CROSS-REFERENCE TO RELATED APPLICATION

This is a U.S. National Phase of PCT Application No. PCT/US2003/033438, filed Oct. 22, 2003, which claims the benefit of U.S. Provisional Application No. 60/420,898, filed Oct. 24, 2002.

STATEMENT OF GOVERNMENT SUPPORT

This invention was made with government support under grant numbers R21GM068993 and 7R01CA075503 awarded by the National Institutes of Health. The government has certain rights in the invention.

BACKGROUND (1) Field of the Invention

The present invention generally relates to regulation of gene expression. More specifically, the invention relates to regulation of gene expression using caged ligands that bind and activate receptors when uncaged by exposure to light.

(2) Description of the Related Art

REFERENCES CITED

Adams, S. R. & Tsien R. Y. (1993) Annu. Rev. Physiol. 55, 755-784.
Albanese, C., Hulit J. Sakamaki, T., & Pestell, R. (2002) Semin. Cell Develop. Biol. 13, 129-141 in press.
Albanese, C., Reutens, A. T., Bouzahzah, B., Fu, M. D'Amico, M., Link, T., Nicholson, R., Depinho, R. A., & Pestell, R. G. (2000) Faseb J. 14, 877-884.
Ando, H., Furuta, T., Tsien, R. Y., & Okamoto, H. (2001) Nature Genetics 28, 317-325.
Arakawa et al. (2001) BMC Biotechnol. 1, 7.
Belshaw, P. J., Spencer, D. M., Crabtree, G. R., & Schreiber, S. L. (1996) Chem. Biol. 3, 731-738.
Chen, J. D. & Evans, R. M. (1995) Nature 377, 454-457.
Cronin, C. A., Gluba, W., & Scrable, H. (2001) Genes Dev. 15, 1506-1517.
Cruz, F. F., Koh, J. T., & Link, K. H. (2000) J. Am. Chem. Soc. 122, 8777-8778.
Curley, K. & Lawrence, D. S. (1999) Cur. Opin. Cell. Biol. 3, 84-85.
Curley, K. & Lawrence, D. S. (1998) J. Amer. Chem. Soc. 120, 8573-8574.
Dinan, L., Hormann, R. E., & Fujimoto, T. (1999) J. Comput. Aided Mol. Des. 13, 185-207.
Feil, R., J. Brocard, B. Mascrez, M. LeMeur, D. Metzger, & P. Chambon (1996) Proc. Natl. Acad. Sci. USA, 93, 10887-90.
Fisher, G. H. et al. (1999) Oncogene 18, 5253-5260.
Furuta et al. (1999) Proc. Natl. Acad. Sci. USA 96, 1193-1200.
Galbraith, M. N. & Horn, D. H. S. (1969) Aust. J. Chem. 22, 1045-1057.
Gingrich, J. R. & Roder, J. (1998) Annu. Rev. Neurosci. 21, 377-405.
Grindley, T. B. (1998) Adv. Carbohydr. Chem. Biochem. 53, 17-142.
Hatchard, C. G., & Parker, C. A. (1956) Proc. R. Soc. London, A220, 518-536.
Huber, R. & Hoppe, N. (1965) Chem. Ber. 98, 2403-2424.
Kaplan, J. H. (1978) Biochemistry 17, 1929-1935.
Liotta, L. A. & Kohn, E. C. (2001) Nature 411, 375-379.
Liu, X., Robinson, G. W., Wagner, K. U., Garrett, L., Wynshaw-Boris, A., & Hennighausen, L. (1997) Genes Dev. 11, 179-186.
Marriott, G. & Walker, J. W. (1999) Trends Plant Sci. 4, 330-334.
Mikitani, K. (1996) Biochem. Biophys. Res. Comm. 227, 427-432.
Monroe, W. T., McQuain, M. M., Chang, M. S., Alexander, J. S., & Haselton, F. R. (1999) J. Biol. Chem. 274, 20895-20900.
Nagashima, N. & M. Ohno (1991) Chem. Pharm. Bull. 39, 1972-1982.
Nagy, A. (2000) Genesis 26, 99-109.
No, D., Yao, T. P., & Evans, R. M. (1996) Proc Natl Acad Sci USA, 93, 3346-3351.
Ormandy, C. J., Camus, A., Barra, J., Damotte, D., Lucas, B., Buteau, H., Edery, M., Brousse, N., Babinet, C., Binart, N., & Kelly, P. A. (1997) Genes Dev. 11, 167-178.
Orsulic, S. et al. (2002) Cancer Cell 1, 53-62.
Pao E. et al. (2003) Proc. Natl. Acad. Sci. U.S.A. 100, 8764-8769.
Petit et al. (1997) Neuron 19, 465-471.
Roskelley, C. D. & Bissell, M. J. (2002) Semin. Cancer Biol. 12, 97-104.
Ryding, A. D., Sharp, M. G., & Mullins, J. J. (2001) J. Endocrinol. 171, 1-14.
Saez et al. (2000) Proc. Natl. Acad. Sci. USA 97, 14512-14517.
Shockett, P. E. & Schatz, D. G. (1996) Proc. Natl. Acad. Sci. USA, 93, 5173-5176.
Sinn, E., Muller, W., Pattengale, P., Tepler, I., Wallace, R., & Leder, P. (1987) Cell 49, 465-475.
Suksamrarn, A., & Pattanaprateep, P. (1995) Tetrahedron 38, 10633-10650.
Wantanable, G., Howe, A., Lee, R. J., Albanese, C., Su, I-W., Karnezis, A. N., Zon, L., Kyriakis, J., Rundell, K., & Pestell, R. G. (1996) Proc. Natl. Acad. Sci. USA 93, 12861-12866.
Wazer, D. E. & Band, V. (1999) Radiat. Oncol. Investig. 7, 1-12.
Walker, J. W. (1988) Methods Enzymol. 172, 288-301.
Wang et al. (1998) Proc. Natl. Acad. Sci. USA 95, 10860-10865.
U.S. Pat. No. 5,635,608.
U.S. Pat. No. 6,258,603.
U.S. Pat. No. 6,333,318.
U.S. Patent Application Publication 20020152493, application Ser. No. 10/005,467, filed Dec. 4, 2001, published Oct. 17, 2002.

Knock-out and knock-in animal models are commonly employed to assess the biological role of specific proteins in the context of a multicellular organism. However, expression of individual genes is a temporal- and spatial (i.e. tissue)-specific phenomenon that can influence both normal and abnormal biological processes. For example, it has not been possible to study the role of certain genes (cyclin D1, Stat5A, prolactin receptor) in mammary gland tumorigenesis because transgenic mice missing these genes lack proper mammary gland development (Sinn et al., 1987; Ormandy et al., 1997; Liu et al., 1997). Indeed, knockouts fail to reproduce a key element that drives carcinogenesis in general, namely the acquisition of somatic mutations in the adult.

To overcome these limitations, systems have been engineered that inducibly regulate the transgene of interest or excise the targeted gene of choice (Ryding et al., 2001; Albanese et al., 2002). These inducible constructs allow gene expression patterns to be temporally controlled during growth and development as well as at any point during the lifespan of the animal. The characteristics of an ideal inducible transgenic system include low basal level expression and robust induction of the transgene, the lack of secondary or deleterious effects of the inducing agent, tissue specific targeting, and the ability to sustain transgene induction. These characteristics are particularly important in the delivery of embryonic lethal, transforming, or otherwise toxic genes. For example, potent oncogenes such as myc exhibit a wide range of biologic effects, and therefore the ability to control both the temporal expression profile and the activity of the gene is critical.

The early inducible transgenic lines relied on the administration of heavy metals or naturally occurring steroid hormones, such as glucocorticoids, to provoke transgene expression (Gingrich & Roder, 1998). However, heavy metals are toxic and glucocorticoids regulate a variety of endogenous genes, thereby complicating interpretation of the biological response to the inducing agent. A variety of additional inducing agents have also been described recently, including tetracycline (tet operon system) (Shockett & Schatz, 1996), IPTG (Lac operon repressor system) (Cronin et al., 2001), FK1012 (FKBP inducible system) (Belshaw et al., 1996), tamoxifen (estrogen receptor system) (Feil et al., 1996), and ecdysone receptor agonists (ecdysone receptor inducible system) (No et al., 1996; Albanese et al., 2000). However, many of these inducible systems are plagued by difficulties such as mosaic induction, toxicity, background transgene expression, sluggish clearance, and poor expression of the transactivator.

In 1996, Evans and his colleagues described an ecdysone-inducible gene expression construct (No et al., 1996). Ecdysone, the insect molting hormone, triggers metamorphosis by binding to and activating the nuclear heterodimer of the ecdysone receptor (EcR) and the product of the ultraspiracle gene (USP). The activated complex, in association with an ecdysone-responsive element (EcRE), subsequently drives gene expression. In the mammalian construct, the EcR and retinoid X receptor (RXR; the mammalian homologue of USP) are constitutively produced. The gene of interest, which is operably linked to the EcRE, is expressed upon introduction of ecdysone (or structurally related analogs). The advantages of this system include low basal expression, high inducibility (up to 4 orders of magnitude), and the fact that ecdysteroids are not toxic and do not affect mammalian physiology.

Inducible gene expression systems, as they are currently devised, provide temporal control over when the gene of interest is activated during the lifetime of the animal. However, fine spatial control over where gene expression is induced is problematic. Studies to date have utilized tissue-selective promoters, such as a modified MMTV promoter construct, to enhance ecdysteroid-induced transgene expression in the mammary gland (Albanese et al., 2000).

Unfortunately, in a very real sense, this technology has limitations, e.g., in cancer studies, because it does not faithfully recapitulate the process of tumorigenesis in the adult. For example, most breast cancers are thought to arise via the oncogenic transformation of epithelial cells that line the mammary ducts followed by clonal expansion (Wazer and Band, 1999). Although tumorigenesis likely proceeds via the transformation of specific individual cell types in anatomically well-defined regions, the relative tumorigenic potential of different mammary precursor cells remains a mystery. Inducible gene expression systems devised to date do not offer the fine spatial control to explore the relationship between tissue microenvironment and the pathogenesis of various disease states.

For these and other reasons, there is a need for methods and genetic constructs that enable fine spacial and temporal control of genetic regulation of genes of interest. The present invention addresses that need.

SUMMARY OF THE INVENTION

Accordingly, the inventors have discovered that spacial and temporal control of expression of genes of interest in a cell can be achieved using certain caged ligands of receptors, for example where the receptor is not naturally present in the species that the cell belongs.

Thus, in some embodiments, the present invention is directed to compounds comprising a ligand that specifically reacts with a first receptor not naturally present in mammals. In these embodiments, the compounds further comprise a molecular cage covalently bound to the ligand that prevents reaction of the ligand with the first receptor, where the ligand in these embodiments is released from the cage and capable of reacting with the first receptor upon exposure of the compound to light.

In other embodiments, the invention is directed to cells of a species, where the cells are transfected with a gene of interest and a gene encoding a first receptor, the gene of interest operably linked to a genetic element capable of being induced by the first receptor when bound to a ligand, and the first receptor not naturally present in the species. In these embodiments, the cells further comprise a compound comprising the ligand and a molecular cage covalently bound to the ligand that prevents reaction of the ligand with the first receptor, where the ligand is released from the cage and capable of reacting with the first receptor upon exposure of the compound to light.

The invention is also directed to methods of expressing a gene of interest in a cell of a species. The methods comprise creating the above-described cells of a species by transfecting the cell with the gene of interest and a gene encoding a first receptor, the gene of interest operably linked to a genetic element capable of being induced by the first receptor when bound to a ligand, the first receptor not naturally present in the species; and adding a compound to the cell, the compound comprising the ligand and a molecular cage covalently bound to the ligand that prevents reaction of the ligand with the first receptor, the ligand capable of being released from the cage upon exposure of the compound to light; then exposing the cells of a species to light sufficient to release the cage from the ligand.

The present invention is additionally directed to methods of expressing a second gene of interest in a cell of a species. The methods comprise transfecting the cell with a first gene of interest and a gene encoding a first receptor, where the first gene of interest encodes a viral receptor, the viral receptor allowing entry of a viral vector into the cell. In these embodiments, the first gene of interest is operably linked to a genetic element capable of being induced by the first receptor when bound to a ligand and the first receptor is not naturally present in the species. The ligand in these embodiments further comprises a molecular cage covalently bound to the ligand that prevents reaction of the ligand with the first receptor, where the ligand is released from the cage and capable of reacting with the first receptor upon exposure of the compound to light. The cell is exposed to the viral vector further comprising an expressible gene encoding the second gene of interest; then the cell is exposed to light sufficient to release the cage from the ligand, allowing the ligand to react with the first receptor, which directs expression of the viral receptor and allows infection of the cell by the viral vector; the second gene of interest is then expressed.

Additionally, the invention is directed to methods of repressing a gene of interest in a cell of a species. The methods comprise transfecting the cell with the gene of interest and a gene encoding a first receptor, the gene of interest operably linked to a genetic element capable of being repressed by the first receptor when bound to a ligand; adding a compound to the cell, the compound comprising the ligand and a molecular cage covalently bound to the ligand that prevents reaction of the ligand with the first receptor, the ligand capable of being released from the cage upon exposure of the compound to light; then exposing the cell to light sufficient to release the cage from the ligand.

In additional embodiments, the invention is directed to methods of inducing elimination of a target sequence in a cell of a species. The methods comprise transfecting the cell with: a gene encoding a recombinase operably linked to a genetic element capable of being induced by a first receptor when bound to a ligand, where the first receptor is capable of inducing the genetic element when the first receptor reacts with a ligand; and a gene encoding the first receptor. The methods further comprise adding a compound to the cell, the compound comprising the ligand and a molecular cage covalently bound to the ligand that prevents reaction of the ligand with the first receptor, where the ligand is capable of being released from the cage upon exposure of the compound to light; and exposing the cell to light sufficient to release the cage from the ligand.

The invention is further directed to kits for the conditional expression of a gene of interest in a cell. The kits comprise, in suitable containers, the compound described above, comprising a ligand that specifically reacts with a first receptor not naturally present in mammals, where the compound further comprises a molecular cage covalently bound to the ligand that prevents reaction of the ligand with the first receptor, wherein the ligand is released from the cage and capable of reacting with the first receptor upon exposure of the compound to light. The kits also comprise a vector comprising a gene encoding the first receptor.

In related embodiments, the invention is also directed to kits for the conditional elimination of a target sequence in a cell. The kits comprise, in suitable containers, one or more vectors comprising a gene encoding a recombinase operably linked to a genetic element capable of being induced by a first receptor when bound to a ligand, where the first receptor is capable of inducing the genetic element when the first receptor reacts with a ligand. The kits also comprise a gene encoding the first receptor, and a compound comprising the ligand and a molecular cage covalently bound to the ligand that prevents reaction of the ligand with the first receptor, where the ligand is released from the cage and capable of reacting with the first receptor upon exposure of the compound to light.

DETAILED DESCRIPTION OF THE INVENTION

Figure 1:
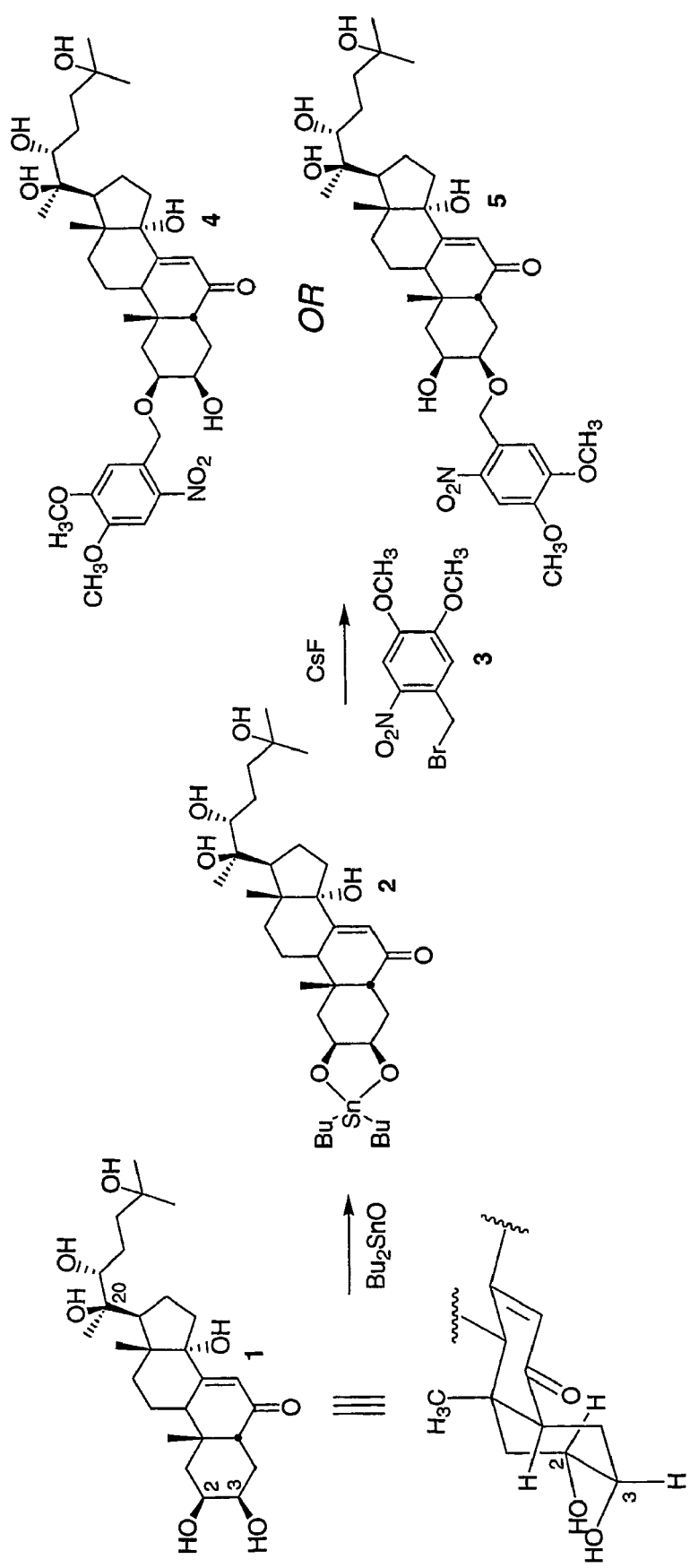
FIG. 1 a schematic depicting a method for synthesis of caged β-ecdysone 4 from β-ecdysone 1.

Abbreviations: COSY, correlation spectroscopy; DQF-COSY, double quantum filtered COSY; EcR, ecdysone receptor; EcRE, ecdysone response element; HMQC, heteronuclear multiple quantum COSY; HSQC, heteronuclear single quantum COSY; RXR, mammalian homologue of USP; USP, ultraspiracle protein.

The present invention is based on the discovery that spacial and temporal control of expression of genes of interest in a cell can be achieved using certain caged ligands of receptors, for example where the receptor is not naturally present in the species that the cell belongs. This discovery enables the use of various compositions and methods to precisely control expression of genes in cells illuminated by light.

Thus, in some embodiments, the invention is directed to compounds comprising a ligand that specifically reacts with a first receptor not naturally present in mammals. In these embodiments, the compound further comprises a molecular cage covalently bound to the ligand that prevents reaction of the ligand with the first receptor, where the ligand is released from the cage and capable of reacting with the first receptor upon exposure of the compound to light.

These compounds are particularly useful for regulating expression of a gene of interest in mammalian cells, including whole animals. Since the first receptor is not naturally present in mammals, expression of the gene of interest by activating the first receptor would not affect other physiological processes in the mammal, as would occur using a naturally occurring first receptor, such as the system described in Cruz et al. (2000). An example of a first receptor not present in mammals is the ecdysone receptor.

As used herein, the term "reaction", "interaction" or "binding", when referring to a ligand-receptor complex, does not connote any particular binding affinity or avidity. It only requires a specific interaction between the ligand and receptor that can cause a change in genetic regulation.

These embodiments are not narrowly limited to ligands that interact with any particular first receptor. They only require that the ligand-receptor interaction results in a change in genetic regulation. For example, the ligand-receptor interaction could result in activation of a factor such as a response element or promoter that controls expression of a gene operably linked to that factor. A non-limiting example of such a ligand-receptor system is the ecdysone-ecdysone receptor-RXR system previously discussed. Alternatively, the ligand-receptor interaction could result in down-regulation of expression of a gene, as occurs, for example with a nuclear co-repressor (Chen & Evans, 1995; Wang et at., 1998). Furthermore, the ligand could be an inhibitor of the first receptor such that its binding inhibits activation of the first receptor by an activating ligand.

In preferred embodiments, the ligand is a small molecule, less than 1000 Dalton. However, the invention also encompasses ligands that are amino acids, oligopeptides, polypeptides, saccharides, lipids, nucleotides, nucleic acids, metal ions, etc. provided the ligand is capable of activating a first receptor not naturally present in mammals. The most preferred ligands are those that, when caged, are capable of passing into a target cell without excessive manipulation such as electroporation or liposome encapsulation.

In some preferred embodiments, the ligand interacts with an ecdysone receptor. The ligand-ecdysone receptor combination is particularly useful in these embodiments because the ecdysone-responsive element (EcRE) allows low basal expression in the absence of the ligand-ecdysone receptor combination, and provides for high induction of the gene of interest when the ligand-ecdysone receptor is present. Additionally, the ligands generally are not toxic and do not affect mammalian physiology. Furthermore, there are many ecdysone receptor activating ligands of disparate structure, allowing for utilization of numerous caging chemistries. Most of the ecdysone receptor ligands are steroids, but others are not. See, e.g., Dinan et al., 1999; Saez et al., 2000; Mikitani, 1996; U.S. Pat. No. 6,258,603. Non-limiting examples include ecdysone, 20-hydroxyecdysone, ponasterone A, muristerone A, inokosterone, 3,5-di-tert-butyl-4-hydroxy-N-isobutyl-benzamide and dibenzoylhydrazines such as tebufenozide and 1,2-dibenzoyl-1-tert-butyl-hydrazine. The skilled artisan would be expected to be able to create an inactive caged version of essentially any ecdysone receptor ligand without undue experimentation.

The invention encompasses the use of any appropriate photolysing molecular cage, now known or later discovered. It is contemplated that the skilled artisan could choose the cage without undue experimentation according to the needs for the individual application. Many different cages are known in the art, and several have been applied to biological molecules. See, e.g., Adams & Tsien, 1993; Curley & Lawrence, 1999; Marriott & Walker, 1999; Furuta et al., 1999; U.S. Pat. No. 5,635,608. These include single photon cages (susceptible to wavelengths of between 300-400 nm, more preferably 325-375 nm, even more preferably 340-360 nm; most preferably about 350 nm—see Example) and two-photon cages (generally susceptible to higher wavelengths, e.g., about 700 nm). The greater efficiency of the latter cages and their susceptibility to higher wavelengths of light that more readily penetrates tissues than single photon cages makes two-photon cages particularly useful where activation of genes of interest is desired in cells that are not on a tissue surface. Nonlimiting examples of two-photon cages include brominated 7-hydrozxycoumarin-4-ylmethyls. See, e.g., Furuta et al., 1999; Pettit et al., 1997.

When the ligand is a steroid, such as a steroid that is an ecdysone receptor ligand (e.g., ecdysone—see Example), a preferred molecular cage is a nitromethoxybenzyl moiety, more preferably a 1-methyl-4,5-dimethoxy-2-nitrobenzene (see FIG. 1).

In other embodiments, the invention is directed to cells of a species that are transfected with a gene of interest and a gene encoding a first receptor, where the gene of interest is operably linked to a genetic element capable of being induced by the first receptor when bound to a ligand, and where the first receptor is not naturally present in the species. In these embodiments, the cells further comprise a compound comprising the ligand and a molecular cage covalently bound to the ligand that prevents reaction of the ligand with the first receptor, wherein the ligand is released from the cage and capable of reacting with the first receptor upon exposure of the compound to light.

As used herein, the term "genetic element" is to be broadly construed as any nucleic acid sequence in the genome of the species that, when interacting with the ligand-receptor, is induced, affecting transcription of the gene of interest. Included are promoters, enhancers, suppressing elements, etc. In this definition, the genetic element is preferably 5', and in close proximity to the gene of interest, such as a promoter. However, the invention encompasses genetic elements that are not physically linked to the gene of interest.

The cells in these embodiments can be of any prokaryotic or eukaryotic species, such as animal cells or plant cells. Because of the applications to human medicine, the animal cells are preferably mammalian cells, most preferably human cells. Preferably, the cells are part of a multicellular organism, since a particular advantage of the invention is the ability to induce the gene of interest in a particular group of cells in a tissue, for example cancer cells, e.g., in a tumor. However, cells in culture, either prokaryotic or eukaryotic cells, are also envisioned as within the scope of the invention. As such, the cells are useful when very synchronous induction of the gene of interest is required, since induction by light is much more synchronous than induction by adding the (uncaged) ligand to a culture because the light inducing system only requires the photolysis of the cage and not the diffusion of the ligand into the cell. The cells of the invention are also useful with cells in culture when induction of the gene of interest is desired in only some of the cells.

In these embodiments, where the cell is part of a multicellular organism, the transfected cells could include one cell or a few cells. However, since spacial control of regulation of the gene of interest is contemplated to be by shining the photolysing wavelengths of light onto the appropriate cells, there does not need to be concern that cells are transfected where the activation of the gene of interest is not desired. Thus, substantially all of the cells of a cell type in the organism, or all the cells of the organism can be transfected with the gene of interest and the first receptor.

It is preferred that the receptor-ligand-genetic element system chosen for these embodiments have minimal basal transcription level of the gene of interest, particularly when expression of the gene of interest in non-target cells is detrimental. In most embodiments, it is also preferred that the difference between the basal transcription level and the induced transcription level is great, preferably at least double, more preferably at least five-fold, even more preferably at least ten-fold, and most preferably at least fifty-fold.

Any receptor-ligand-genetic element system not naturally present in the species can be used in these embodiments. Selection of such a system is within the skill of the art, without undue experimentation. In species not having the ecdysone receptor, e.g., mammals or bacteria, the ecdysone/ecdysone receptor/ecdysone-response element is generally preferred.

In some preferred embodiments, particularly when the cell is a vertebrate (e.g., mammalian) cell, the compound is one of the previously described compounds. However, the invention is not limited to those compounds that comprise ligands to receptors not naturally present in mammals. The skilled artisan would understand that the invention would be useful for controlling expression of genes of interest in cells of virtually any species, with any first receptor that induces transcription upon interaction with a ligand.

The genetic element capable of being induced by the first receptor is preferably not inducible by another receptor that could be present in the transfected cell. To prevent side effects of the light induction (e.g., altered transcription of genes that are not the gene of interest), it is also preferred that the genetic element is not also naturally present in the cell that is exposed to the photolysing light. The genetic element can also be naturally occurring or genetically manipulated, e.g., to affect the basal or induced transcription rates.

In embodiments where the first receptor requires two or more proteins, such as the ecdysone receptor, genes for both proteins could be provided transgenically. Such a case is useful, e.g., if the RXR/USP component of the ecdysone receptor is not naturally present in the cell, is present in limiting amounts, or unexpectedly poorly interacts with the EcR and ligand.

Where the ecdysone receptor and an ecdysone receptor ligand is used, an ecdysone receptor from any species having such receptors can be used. The skilled artisan could identify a previously unidentified ecdysone receptor gene, and isolate and genetically manipulate that gene without undue experimentation using known methods and present knowledge about other ecdysone receptor genes.

The gene of interest that can be transfected into the cells of the present invention is not limited to any particular type of gene, and includes both genes that can be translated (into oligopeptides or polypeptides) as well as useful genes that encode an untranslated RNA such as an antisense gene, an aptamer, or an siRNA, of which there are myriad examples known in the art. Nonlimiting examples of translatable genes that could be useful in the present invention include genes encoding apoptosis-inducing proteins, proteins comprising an antibody binding domain, angiogenic factors, cytokines, viral receptors, blood proteins, transcription factors, structural proteins, viral proteins, bacterial proteins, other extracellular proteins, proteins already present in the cell (for the purpose of, e.g., overexpressing the protein), and engineered proteins with no natural counterpart.

In some embodiments, the gene of interest encodes a recombinase such that, upon light induction, the recombinase is synthesized, causing elimination of a target sequence. The recombinase can be any recombinase now known or later discovered that could be used for this purpose. Nonlimiting examples include Cre recombinase, flp recombinase, Int recombinase, TpnI and β-lactamase transposons, Tn3 resolvase, SpoIVC recombinase, Hin recombinase, and Cin recombinase. See, e.g., discussion in U.S. Patent Application Publication 20020152493 at paragraph 66, and the references cited therein, all incorporated by reference. A preferred recombinase is Cre recombinase, because of its precision and ease of use (Nagy, 2000). Where the recombinase is a Cre recombinase, the target sequence is flanked by two loxP sites (Id). As used herein, a loxP site is a sequence consisting of two 13 bp inverted binding sites separated by a 8 bp spacer. The wild-type loxP sequence (ATAACTTCGTATAATGTAT-GCTATACGAAGTTAT) can be used, or any known loxP mutants, such as those which are designed to prevent the presence of a residual loxP site after recombination (see, e.g., Arakawa et al., 2001).

In the embodiments where the gene of interest is a recombinase, the invention is not limited to any particular target sequence to be eliminated. Nonlimiting examples of a useful target sequence include a target sequence comprising a promoter, such that elimination of the target sequence prevents a gene operably linked to the target sequence from being transcribed, or a target sequence comprising a gene (including translatable genes and nontranslated genes, e.g., those encoding antisense RNA, aptamers, or siRNA) which would be eliminated upon exposure to the photolysing light. Thus, the constructs where the gene of interest is a recombinase can be used to permanently eliminate the expression of a particular gene, only in the cells exposed to the photolysing light wavelengths.

In alternative nonlimiting embodiments, the target sequence is 3' from a promoter, such that when the target sequence is eliminated by the recombinase, the promoter becomes operably linked to a second gene of interest, thus inducing the second gene of interest upon exposure of the cell to the photolysing light. In these embodiments, the second gene of interest can be any gene, including a gene encoding an untranslated RNA or a translatable gene. Thus, the recombinase gene of interest can be used to permanently induce expression of a second gene of interest. This is opposed to embodiments where the gene of interest is not a recombinase, since the induction by the uncaged ligand usually only temporarily induces expression of the gene of interest. See, e.g., Example 1, where expression induced by the ecdysone receptor had a half-life of about 16 hours.

The embodiments where the gene of interest is a recombinase that causes operable linkage of a promoter with a second gene of interest is not limited to any particular type of promoter, and could include any inducible or a constitutive promoter, as needed.

Another non-limiting example of a construct allowing permanent induction of the second gene of interest is one where the target sequence comprises a stop codon, such that light induction of the recombinase eliminates the stop codon and puts the coding region of the gene in frame, allowing transcription of the complete protein encoded by the second gene of interest.

In embodiments where the gene of interest is a viral receptor, preferred viral receptors are viral receptors that allow entry of a viral vector into the cell. In so doing, a second gene of interest can be provided by the viral vector that has been engineered to further comprise the second gene of interest. By this method, any second gene of interest can be conveniently expressed in the illuminated cells by providing the viral vector comprising the desired second gene of interest. This method requires only one target organism, transfected with the first receptor and the viral receptor operably linked to a genetic element capable of being induced by the first receptor when bound to a ligand, and, since any gene of interest can be easily expressed in the cells of the organism by (a) adding the caged ligand and the viral vector comprising the gene of interest, and (b) illuminating the targeted cells. Upon such illumination, the ligand is uncaged, allowing its binding to the first receptor, which then allows expression of the viral receptor. Expression of the viral receptor then allows entry of the virus into those illuminated cells, and expression of the gene of interest from the viral vector. Thus, the gene of interest engineered into the viral vector is only expressed in the illuminated cells. A nonlimiting example of such a viral vector and viral receptor is the TVA receptor and subgroup A avian leucosis virus, for example comprising an RCAS vector. See Orsulic et al., 2002; Fisher et al., 1999; Pao et al., 2003.

The above cells, already exposed to light and the viral vector expressing the second gene of interest, where the viral vector has infected the cell and expresses the second gene of interest, are also contemplated as being within the scope of the invention.

In these embodiments, the second gene of interest is not limited to any particular gene. As with previous embodiments, preferred second genes of interest encode apoptosis-inducing proteins, proteins comprising an apoptosis-inducing protein, proteins comprising an antibody binding domain, angiogenic factors, cytokines, blood proteins, transcription factors, structural proteins, viral proteins, bacterial proteins, extracellular proteins, proteins already present in the cell, and engineered proteins with no natural counterpart. The second gene of interest can also encode an untranslated RNA, for example an antisense RNA, an aptamer, and an siRNA.

The invention is not limited to any particular method of transfecting the cells with the gene of interest and the gene encoding a first receptor. The gene of interest could be on the same or on different vectors as the gene encoding the first receptor. The vectors used can also be any vector appropriate for the cell being transfected, and include viral vectors and naked DNA vectors such as plasmids. The skilled artisan would generally be expected to determine, without undue experimentation, suitable transfection vectors and methods for any particular cell.

The invention also encompasses the use of transfection methods and vectors that allow stable as well as transient expression of the first receptor; extrachromosomal as well as chromosomally integrated (either by homologous or heterologous recombination) transfection of the cell is also envisioned. The cells of the invention could also be descended from a transfected cell, for example a cell from a transgenic organism whose germ line was transfected with the gene of interest and/or the gene encoding a first receptor; or the progeny of such an organism.

The compound can enter the cell by any means appropriate, as could be determined by the skilled artisan without undue experimentation. It would be expected that the compound might degrade or otherwise become inactive in the cell over time. The skilled artisan would understand that the rate of such degradation would depend on the chemical stability of the compound as well as the presence in the cell of enzymes that could degrade the compound.

The present invention is also directed to methods of inducing a gene of interest in a cell of a species. The methods comprise, first, creating any of the above described cells. The cells are created in two steps, which could be performed in any order. One step is transfecting the cell with the gene of interest and a gene encoding a first receptor, where the gene of interest is operably linked to a genetic element capable of being induced by the first receptor when bound to a ligand, and the first receptor is not naturally present in the species. The other step is adding a compound to the cell, where the compound comprises the ligand and a molecular cage covalently bound to the ligand that prevents reaction of the ligand with the first receptor, the ligand capable of being released from the cage upon exposure of the compound to light. The cell is then exposed to light sufficient to release the cage from the ligand.

In preferred embodiments, the cell in these methods is part of a living multicellular organism, where some or all of the cells can be transfected with the gene of interest and the first receptor.

The light used to release the cage from the ligand must include wavelengths appropriate and of sufficient intensity to cause uncaging of the cage from the ligand. For example, where the cage is a single photon cage, the light preferably comprises wavelengths at 300-400 nm; more preferably at 325-375 nm. Alternatively, where the cage is a two-photon cage, the light generally must comprise wavelengths of about 600-800 nm, more preferably 650-750 nm, most preferably about 700 nm.

As previously discussed in the context of the cells of the invention, the transfection of the cell can be by any appropriate means, using any appropriate vector type, etc. Additionally, these methods include the use of transgenic cells descended from a transfected cell, for example a cell from a transgenic organism whose germ line was transfected with the gene of interest and/or the gene encoding a first receptor; or the progeny of such an organism. Other parameters previously discussed in the context of the cells of the invention also applies to the cells useful for these methods.

The skilled artisan would understand that these methods are particularly useful for inducing a gene in a cell or cells at a precise location, e.g., in a tissue such as cancerous tissue in a mammal, for example a human cancer patient. Since the first receptor is not normally present in the species, the activation of the first receptor by uncaging the compound would not be expected to cause altered transcription other than of the gene of interest.

Where the gene of interest is a recombinase such as a Cre recombinase, as previously described in the context of the cells of the invention, a target sequence is permanently eliminated only from the cells exposed to photolysing light. Depending on the design of the genetic construct transfected into the cell, the elimination of the target sequence can have the effect of permanently eliminating expression of a second gene of interest (e.g., if the target sequence encodes the gene or a genetic element for the gene), inducing expression of a second gene of interest (e.g., if eliminating the target sequence eliminates a stop codon, preventing translation of the complete second gene of interest), or permanently altering expression of the second gene of interest (e.g., if eliminating the target sequence eliminates one promoter operably linked to the second gene of interest and operably links the second gene of interest with a second promoter with different expression parameters than the first promoter). These methods are entirely within the skill of the art. Furthermore, a skilled artisan could design other constructs with useful effects as necessary for any particular application.

The present invention is additionally directed to methods of expressing a second gene of interest in a cell of a species, utilizing a viral vector-viral receptor expression system. The methods comprise transfecting the cell with a first gene of interest and a gene encoding a first receptor, where the first gene of interest encodes a viral receptor, the viral receptor allowing entry of a viral vector into the cell. In these embodiments, the first gene of interest is operably linked to a genetic element capable of being induced by the first receptor when bound to a ligand and the first receptor is not naturally present in the species, as described above. The ligand in these embodiments further comprises a molecular cage covalently bound to the ligand that prevents reaction of the ligand with the first receptor, where the ligand is released from the cage and capable of reacting with the first receptor upon exposure of the compound to light as described above. The cell is exposed to the viral vector further comprising an expressible gene encoding the second gene of interest. The cell is then exposed to light sufficient to release the cage from the ligand, allowing the ligand to react with the first receptor, which directs expression of the viral receptor and allows infection of the cell by the viral vector. The second gene of interest is then expressed.

A preferred example of the viral receptor-viral vector system utilizes the TVA receptor for subgroup A avian leucosis virus, and the viral vector is a subgroup A avian leucosis virus, as described in the context of the cells of the invention, and in Orsulic et al., 2002, Fisher et al., 1999, and Pao et al., 2003. That system is preferred because the RCAS vector utilized therein is flexible and well developed.

A preferred first receptor is an ecdysone receptor, and some preferred ligands are steroids, particularly when the first receptor is an ecdysone receptor. Preferred examples of steroid ligands for the ecdysone receptor are ecdysone, 20-hydroxyecdysone, ponasterone A, muristerone A, inokosterone, 3,5-di-tert-butyl-4-hydroxy-N-isobutyl-benzamide and a dibenzoylhydrazine.

As with other embodiments, the second gene of interest can be operably linked to an inducible promoter or a constitutive promoter. Nonlimiting examples of preferred second genes of interest are genes encoding an apoptosis-inducing protein, a protein comprising an apoptosis-inducing protein, a protein comprising an antibody binding domain, an angiogenic factor, a cytokine, a blood protein, a transcription factor, a structural protein, a viral protein, a bacterial protein, an extracellular protein, a protein already present in the cell, or an engineered protein with no natural counterpart. Alternatively, the second gene of interest can encode an untranslated RNA, for example an antisense RNA, an aptamer, or an siRNA.

The invention is additionally directed to methods of repressing a gene of interest in a cell of a species. These methods comprise transfecting the cell with the gene of interest and a gene encoding a first receptor, the gene of interest operably linked to a genetic element capable of being repressed by the first receptor when bound to a ligand; adding a compound to the cell, the compound comprising the ligand and a molecular cage covalently bound to the ligand that prevents reaction of the ligand with the first receptor, the ligand capable of being released from the cage upon exposure of the compound to light; then exposing the cell to light sufficient to release the cage from the ligand.

These methods are not narrowly limited to any particular repressing first receptor. Examples of some such useful first receptors include transcriptional co-repressors (Chen & Evans, 1995; Wang et al., 1998). Preferably, in these embodiments, the first receptor is not naturally present in the species, to prevent undesirable side effects caused by the induction.

These methods are entirely analogous with the previously described methods of inducing a gene of interest, except a repressing first receptor, rather than an inducing first receptor, is used. Thus, the cells can be prokaryotic or eukaryotic; they can also be part of a living multicellular organism; the gene of interest can be any translatable or non-translatable gene, etc.

These embodiments are useful where the induction of a gene is not desired at particular times and/or places (e.g., in particular cells of a tissue, such as cancer cells). In some embodiments, the gene of interest is one that is normally present under native regulation (e.g., under the control of a native constitutive or inducible promoter), and gene of interest and the genetic element capable of being repressed by the first receptor is transfected into the cell by homologous recombination. Exposing such a cell to light would thus repress the native gene. Other applications of these methods would be readily apparent to the skilled artisan.

In related embodiments, the invention is also directed to methods of inducing elimination of a target sequence in a cell of a species. These methods comprise transfecting the cell with: a gene encoding a recombinase operably linked to a genetic element capable of being induced by a first receptor when bound to a ligand, where the first receptor is capable of inducing the genetic element when the first receptor reacts with a ligand; and also transfecting the cell with a gene encoding the first receptor. The methods also comprise adding a compound to the cell, the compound comprising the ligand and a molecular cage covalently bound to the ligand that prevents reaction of the ligand with the first receptor, where the ligand is capable of being released from the cage upon exposure of the compound to light. After the above steps, the cell is exposed to light sufficient to release the cage from the ligand.

As with previously described embodiments, a preferred recombinase is Cre recombinase. In those embodiments employing a Cre recombinase, the cell must also be transfected with two loxP sites flanking the target sequence. The scope of the various aspects of these embodiments have been discussed infra, in the context of other methods and compositions.

The invention is additionally directed to kits for the conditional expression of a gene of interest in a cell. The kits comprise, in suitable containers, the compounds described above that comprises a ligand that specifically reacts with a first receptor not naturally present in mammals, where the compound further comprises a molecular cage covalently bound to the ligand that prevents reaction of the ligand with the first receptor, and where the ligand is released from the cage and capable of reacting with the first receptor upon exposure of the compound to light. The kits also comprise a gene encoding the first receptor.

These kits can comprise components that are particularly useful for the viral receptor-viral vector system described above. For example, the first vector of the kit can comprise a gene encoding a viral receptor, where the viral receptor allowing entry of a viral vector into a cell, and the kit can also comprise the viral vector comprising a site for insertion of the gene of interest such that the gene of interest can be expressed when the viral vector infects the cell. As discussed above in the context of the cells of the invention, a preferred viral receptor-viral vector combination is a TVA receptor for subgroup A avian leucosis virus and a subgroup A avian leucosis virus vector. In these embodiments, the gene of interest can be operably linked to an inducible promoter or a constitutive promoter.

The kits can be directed to be used with any prokaryotic, eukaryotic or archaeal cell. In some preferred embodiments, the cell is a mammalian cell. It is also preferred that the cell is part of a multicellular organism.

The kits can optionally comprise instructions for expressing the gene of interest in the cell transfected with the vector when the cell is exposed to the compound and light.

Also within the scope of the invention are kits that facilitate executing the methods of eliminating a target sequence in a cell described above. These kits comprise, in suitable containers, one or more vectors comprising (a) a gene encoding a recombinase operably linked to a genetic element capable of being induced by a first receptor when bound to a ligand, where the first receptor is capable of inducing the genetic element when the first receptor reacts with a ligand; and (b) a gene encoding the first receptor. The kits also comprise a compound comprising the ligand and a molecular cage covalently bound to the ligand that prevents reaction of the ligand with the first receptor, where the ligand is released from the cage and capable of reacting with the first receptor upon exposure of the compound to light.

As discussed above in the context of the methods of eliminating a target sequence, a preferred recombinase is a Cre recombinase. Also, the first receptor is preferably an ecdysone receptor, and some preferred ligands are steroids, particularly when the first receptor is an ecdysone receptor. Preferred examples of steroid ligands for the ecdysone receptor are ecdysone, 20-hydroxyecdysone, ponasterone A, muristerone A, inokosterone, 3,5-di-tert-butyl-4-hydroxy-N-isobutyl-benzamide and a dibenzoylhydrazine. These kits also optionally comprise instructions for using the kit to eliminate a target sequence in cells transfected with the vectors and exposed to the compound and to light.

Preferred embodiments of the invention are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example

Spacial and Temporal Gene Regulation using Caged β-Ecdysone

Example Summary

Transgene-based inducible expression systems furnish the means to study the influence of any gene of interest at any point during an organism's lifetime. This powerful technology adds a temporal dimension to the existing knockout strategies commonly employed to assess protein function in vivo. However, in biological systems, the expression of individual genes is both temporally and spatially (i.e. cell/tissue)-regulated. Consequently, an experimental methodology that furnishes both temporal and spatial control over transgene expression would provide the additional spatial dimension to assess protein function in the context of tissue microenvironment. We describe herein the creation and study of a light-activatable counterpart to the previously reported ecdysone-inducible gene expression system. A stannylene acetal-based strategy was employed to prepare the first example of a caged ecdysteroid. The latter is nearly inactive as an inducing agent in a luciferase-based gene expression system. However, upon exposure to brief illumination, the caged ecdysteroid is rapidly converted into active β-ecdysone. We have found that the caged β-ecdysone is cell permeable, can be intracellularly photouncaged and, in combination with spot illumination, can be used to drive spatially discrete protein expression in a multicellular setting. Thus, we describe herein a light-activatable form of ecdysone and its application to the spatial regulation of gene expression.

Materials and Methods

General. β-ecdysone was purchased from A. G. Scientific. All other reagents and solvents were purchased from Aldrich. Silica gel 60 (40 µm, Baker) was employed for column chromatography. 1-D NMR spectra were recorded on a Bruker DRX-300 and 2-D spectra on a Bruker DRX-600. Chemical shifts are reported downfield from tetramethylsilane.

Preparation of Caged β-ecdysone 4. See FIG. 1. A suspension of β-ecdysone (20 mg, 41.6 µmol) and dibutyltin oxide (13.5 mg, 54.2 µmol) in anhydrous methanol (5 mL) was heated to reflux for 3 hr under argon. After the solvent was removed under reduced pressure, the residue was subsequently azeotroped with anhydrous benzene (3×2 mL). The resulting stannylene acetal was further dried in vacuo for 2 hr before addition of 3 Å molecular sieves (100 mg), CsF (25.2 mg, 166.4 µmol), 1-bromomethyl-4,5-dimethoxy-2-nitrobenzene 3 (20.6 mg, 74.9 µmol), and anhydrous DMF (1 mL). After the reaction mixture was stirred at room temperature overnight, the solvent was evaporated under reduced pressure. The resulting residue was purified by silica gel column chromatography (methylene chloride/methanol: 6/1) to afford 4 as an off-white solid (25.3 mg, 90%). The purity was determined to be >99% by analytical HPLC (retention time 16.2 min on a Vydac C4 column 250 mm×3.0 mm; monitored at 242 nm: a 15 min linear gradient from 95% A (water) to 50% B (acetonitrile) followed by 50% B for 5 min with the flow rate of 1 mL/min). $^1$H-NMR (300 MHz, CD3OD): δ 0.89 (s, 3H), 0.99 (s, 3H), 1.19 (s, 9H), 1.20-1.98 (m, 17H), 2.39 (m, 2H), 3.11 (m, 1H), 3.72 (m, 1H), 3.90 (s, 3H), 3.97 (s, 3H), 4.25 (br s, 1H), 4.99 (q, 2H), 5.81 (d, 1H), 7.42 (s, 1H), 7.71 (s, 1H). HRMS (ESI+) Calcd for $C_{36}H_{54}NO_{11}$: 676.3697 Found: 676.3674. A series of 2-D correlation (COSY) NMR experiments were subsequently performed to assess the site of alkylation on the β-ecdysone framework, including double quantum filtered COSY (DQF-COSY), heteronuclear single quantum correlation (HSQC), and heteronuclear multiple quantum correlation (HMQC) spectroscopies.

Photolysis of Caged β-ecdysone 4. A 500 µL 100 µM solution of 4 in 2% methanol/98% water was placed in a 24-well culture plate. Photolysis was performed using an Oriel 200 W Hg arc lamp (model 6283) with a 348 nm filter (Oriel, lot number 51260; 50% internal transmittance at 348 nm and cutoff at 325 nm) to remove short wavelength light and an IR filter to remove heat. Aliquots of 10 µL were removed at different time points of photolysis and were analyzed by analytical HPLC (monitored at 242 nm) employing a Vydac C4 (250 mm×3.0 mm) column and using the following solvent system: a linear gradient from 95% A (water):5% B (acetonitrile) to 50% A (water):50% (acetonitrile) over 15 min followed by 50% A (water):50% B (acetonitrile) for 5 min with flow rate at 1 mL/min.

Plasmid Description. The luciferase reporter (E/GRE)$_6$TK81LUC consists of multimeric E/GRE binding sites from (E/GRE)$_4$ΔMTVLuc linked to the minimal TK promoter in the pA$_3$LUC reporter plasmid. The modified MMTV promoter from MMTVp206 that incorporates the 5'UTR of v-Ha-ras was inserted into a vector containing a modified ecdysone receptor VgEcR (a gift from R. Evans) to form MMTV-VgEcR.

Cell Culture, DNA Transfection, and Luciferase Assays. Cell culture, DNA transfection, and luciferase assays were performed as previously described (Wantanable et al., 1966). Briefly, 293-derived BOSC cells (293T) were seeded into individual wells of a 24 well plate and maintained in Dulbecco's modified Eagles medium with 10% fetal calf serum and 1% penicillin/streptomycin. Cells were transiently transfected with pVgEcR/RXRα and (E/GRE)$_6$TKLUC via a standard calcium phosphate method. The media was changed after 14 hr and the cells treated with 10 µL of 5 mM β-ecdysone 1 (FIG. 1) in methanol (to furnish a 100 µM final concentration of ecdysteroid). Cells were either left un-illuminated or illuminated for 1 min using an Oriel 200 W Hg arc lamp (model 6283) with a 348 nm filter (Oriel, lot number 51260, 50% internal transmittance at 348 nm and cutoff at <325 nm) to remove short wavelength light and two IR filters to remove heat. Cells were subsequently lysed as previously described and the luciferase assay performed at room temperature using an Autolumat LB 953 (EG & G, Berthold). Luciferase content was measured by calculating the light emitted during 10 sec of the reaction. The values are expressed in arbitrary light units.

Time-dependent luciferase assays. 293T cells were split in a 24-well culture plate (Becton Dickinson Labware, lot #353047) and were transfected by a calcium phosphate method. The cells in 500 μL culture medium were incubated with either 100 μM caged β-ecdysone, 100 μM β-ecdysone, or absent an ecdysteroid ligand. After the cells were incubated with caged β-ecdysone for 16 hours, the medium was removed and washed with PBS once. A fresh medium free of ligand was then immediately added just prior to UV light exposure for 1 min. In the "Caged+hv" experiment, the caged β-ecdysone ligand remained in the medium and these cells were likewise illuminated for 1 min. Cells that were not exposed to ecdysteroid ligand were treated in an otherwise analogous fashion. The cells were then returned to the incubator for various time intervals. Incubation was terminated by treating cells with an extraction buffer (1% Triton X-100 and 1 mM DTT in GME). Luciferase activity was preformed as described above.

Immunodetection of Intracellularly Expressed Luciferase. 293T cells were transferred to the individual wells of a 24-well culture plate (Becton Dickinson Labware, lot #353047) and transfected as described above. The cells were then incubated with either 100 μM β-ecdysone or 100 μM caged β-ecdysone for 16 hr. The medium was removed and the cells washed once with PBS before addition of an ecdysteroid free medium. The surface of the pre-scored wells was spot illuminated (~0.25 $mm^2$) for 10 sec on a light microscope using a 100 W Hg-Arc lamp through an Olympus UAPO 20×/0.40 objective. The cells were then incubated for 6 hr, fixed with 4% formaldehyde in PBS for 60 min, washed with PBS 3×5 min, permeabilized with 0.1% TritonX100 for 10 min, washed with PBS 3×5 min, and blocked with 1% normal donkey serum (Jackson ImmunoResearch catalog #017-000-121) in PBS for 45 min. The cells were subsequently exposed to 300 μL of anti-luciferase pAb (polyclonal goat antibody, Promega, lot #149040) at a concentration of 40 μg/mL in 1% donkey serum in PBS. After incubation for 2 hr at room temperature in a humidified chamber, the cells were washed with PBS 3×15 min and exposed to 300 μL of an Alexa Fluor 568-labeled rabbit anti-goat IgG (20 μg/mL in 1% donkey serum/PBS for 1 hr, Molecular Probes, catalog #A-11079). Unbound antibody was removed by washing with PBS 3×15 min and the cells treated with 300 μL of mounting medium (N-propyl gallate at 6 mg/mL in 1:1 glycerol:PBS). Images were taken using an Olympus IX-70 microscope equipped with a CCD camera.

Results

Synthesis and Characterization of Caged β-Ecdysone 4. We initially sought to prepare a biologically inactive form of β-ecdysone 1 that, upon photolysis, would furnish the active ecdysteroid. A wide variety of ecdysteroid derivatives have been reported and, in general, the presence of free hydroxyl groups at the C-2, C-3, and C-20 positions are required for biological activity (Dinan et al., 1999) (FIG. 1). Consequently, we envisioned that modification of one (or more) of these alcohol moieties with a photosensitive substituent should furnish an inactive ecdysteroid analog that ultimately could be "switched-on" using high intensity light. An alkylated, as opposed to an acylated, ecdysone would enjoy the advantage of enhanced biological stability. However, to the best of our knowledge, we know of no report describing the alkylation of any of the hydroxyl functionalities on ecdysone or its structurally related congeners. Indeed, our initial attempts to alkylate β-ecdysone with the caging agent 3 failed to furnish a modified ecdysteroid derivative (e.g. acetonitrile/N-methyl morpholine/3).

The acetonide of the C-2/C-3 diol has been described (Suksamrarn & Pattanaprateep, 1995) and consequently we wondered whether the corresponding tin acetal 2 could be formed in situ. Tin-based acetal intermediates have been extensively employed in carbohydrate chemistry to furnish monosubstituted derivatives in high yield and high regioselectivity (Grindley, 1998). Although the dibutylstannylene acetal 2 appeared to form with ease, attempted alkylation with 3 furnished the desired monoalkylated product in only 12% yield. We subsequently discovered that 3 is prone to decomposition in the presence of base ($KHCO_3$, $Et_3N$). Although alkylation of stannylene acetal alcohol moieties generally requires fairly vigorous conditions, there have been reports that added nucleophiles promote the desired reaction under mild conditions (Nagashima & Ohno, 1991). Indeed, we obtained a single monoalkylated β-ecdysone (high resolution mass spectrometry and a single peak by HPLC) in 90% yield when the alkylation was conducted in the presence of CsF. Previous studies using a variety of acylating agents suggest that the 2-OH of ecdysteroids is by far the most reactive of the hydroxyl moieties on the ecdysteroid nucleus (Dinan et al., 1999). In addition, extensive studies with a multitude of cis-1,2-diol tin acetal-monosaccharide intermediates revealed that the preferred site of alkylation proceeds (often exclusively) at the equatorial hydroxyl group (Grindley, 1998).

Figure 2:
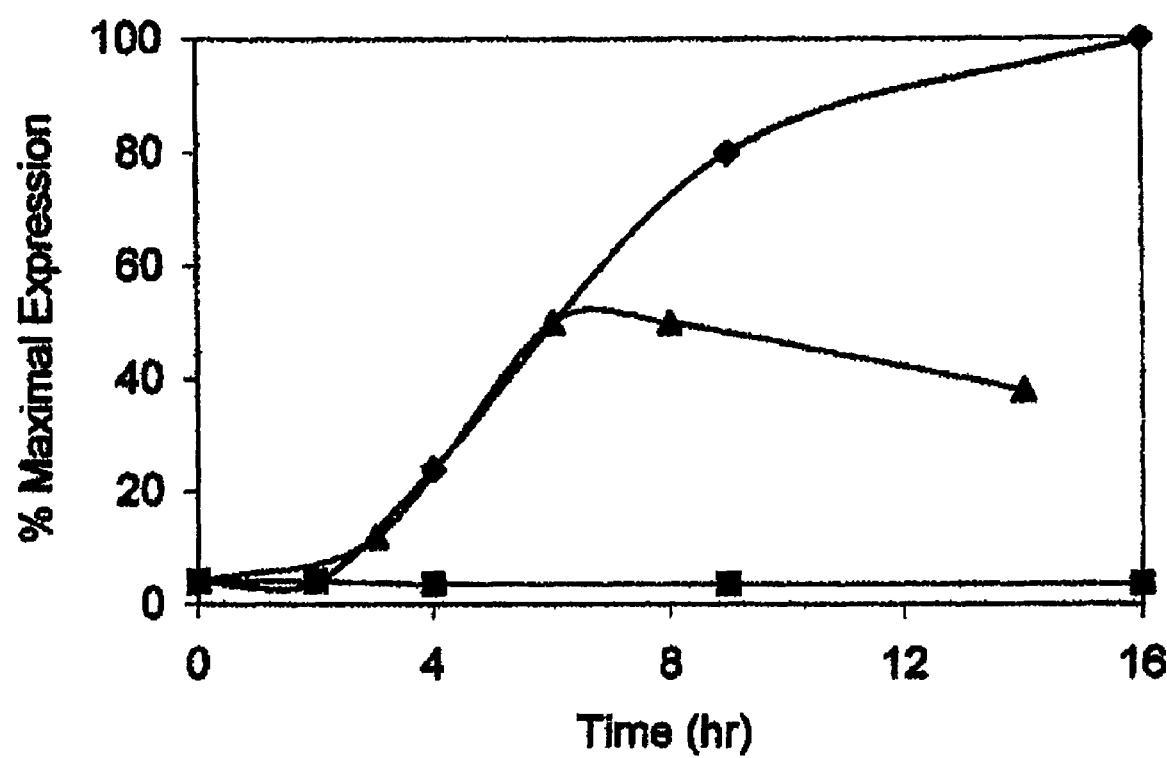
FIG. 2 shows NMR spectra described in the Example. Panel (a) shows the 1-D $^1$H NMR spectrum of β-ecdysone 1 (upper) and caged β-ecdysone 4 (lower). The alkylation induced change in the chemical shift of the C-3 proton is highlighted. Panel (b) shows the HMBC 2-D spectrum of caged β-ecdysone 4. Long range coupling between the benzylic methylene protons ($CH_2$) of the dimethoxy-nitrobenzyl substituent and the C-2 carbon is present. By contrast, no such coupling is observed between $CH_2$ and the C-3 carbon.

The 3-dimensional structure of ecdysone has been described and its stereochemical rendering is shown adjacent to 1 in FIG. 1 (Huber & Hoppe, 1965). The methyl substituent at the ring A/ring B junction lies axial relative to the B ring, but equatorial relative to ring A. Consequently, the C-2 and C-3 hydroxyl moieties are arranged equatorially and axially, respectively, on ring A. Based upon these considerations, we predicted that alkylation should occur predominantly, if not exclusively, at the C-2 alcohol to furnish 4. However, an examination of the $^1H$ NMR spectrum, in combination with previously reported proton chemical shifts (Galbraith & Horn, 1969), suggested that alkylation may have transpired at the C-3 hydroxyl position (Albanese et al., 2000). The latter conclusion arises from the obvious alkylation-induced chemical shift of the C-3 hydrogen (FIG. 2a). Given the difference between the predicted (4) and the apparent products (5) (FIG. 1), we obtained the complete $^1H$ and $^{13}C$ chemical shift assignments for β-ecdysone using a combination of $^1H$-$^1H$ (DQF-COSY), shortrange $^1H$-$^{13}C$ (HSQC), and long-range $^1H$-$^{13}C$ (HMBC) correlation NMR spectroscopies. The HMBC spectrum of the caged β-ecdysone 4 reveals an obvious coupling between the benzyl methylene protons of the photolabile substituent and the carbon at the C-2 position on the ecdysteroid nucleus (FIG. 2b). By contrast, no such coupling is observed between the benzyl methylene protons and the C-3 carbon. Therefore, we conclude that alkylation proceeds at the C-2 hydroxyl to furnish 4. The most dramatic alkylation-induced change in the 1-D spectrum (FIG. 2a), namely the chemical shift of the C-3 proton, is best rationalized by invoking a deshielding effect induced by the adjacent C-2 hydroxyl benzyl substituent.

Photoconversion of Caged β-Ecdysone 4 to β-Ecdysone 1. A preliminary assessment of the light-induced conversion of the caged analog 4 to β-ecdysone 1 was performed using a 24-well plate system. Wells in the plate were selectively photolyzed for various time intervals using a Hg arc lamp. Aliquots from the wells were subsequently analyzed by HPLC to assess formation of 1 (data not shown). A maximal photoconversion of 60% was achieved after 1 min of photolysis.

Longer periods of photolysis did not improve the overall yield of photoconversion. The photochemical quantum yield ($\phi=0.034$) was determined using ferrioxalate actinometry (Hatchard & Parker, 1956) according to the equation $\phi=\Delta P/(I \times t)$, where t is the irradiation time, $\Delta P$ is the amount of photolabile converted, and was determined using HPLC peak areas.

Light-Driven Luciferase Expression in Transiently Transfected 293T Cells. We employed a luciferase-based expression system to examine the biological activity of β-ecdysone and its alkylated analog 4. The 293T cell line was transiently transfected to constitutively express EcR/RXR and inducibly express (upon exposure to β-ecdysone) luciferase. Compound 4 was added to the transfected 293T cells, the cell culture subsequently illuminated, and luciferase activity assessed (Table 1). There is little observable luciferase activity with culture media alone. Exposure of the cells to the bioactive β-ecdysone 1 generates a nearly 90-fold induction of luciferase. By contrast, the caged analog 4 furnishes a slight 6-fold induction of activity over that of culture media alone. However, 1 min photolysis of cells treated with 4 induces a dramatic enhancement of luciferase formation, which is approximately 60% of the expression displayed by the bioactive species 1. The latter is consistent with our observation that a 1 min photolysis time window converts approximately 60% of the caged derivative 4 into its bioactive counterpart 1. Finally, illumination in the absence of ligand fails to induce luciferase production. These experiments demonstrate that light can be used to activate the EcR/RXR gene expression system.

TABLE 1

Luciferase expression in 293T cells transiently transfected with plasmids that code for constitutively expressed EcR/RXR and inducibly expressed luciferase in the presence and absence of -ecdysone 1 or its caged analogue 4.

| Experimental Conditions | Fold luciferase induction |
| --- | --- |
| Culture media/2% MeOH | — |
| β-ecdysone 1/culture media/2% MeOH | 88 ± 9 |
| caged β-ecdysone 4/culture media/2% MeOH | 6.5 ± 0.1 |
| caged β-ecdysone 4/culture media/2% MeOH/1 min hv | 50 ± 4 |
| Culture media/2% MeOH/1 min hv | 0.9 ± 0.1 |

Figure 3:
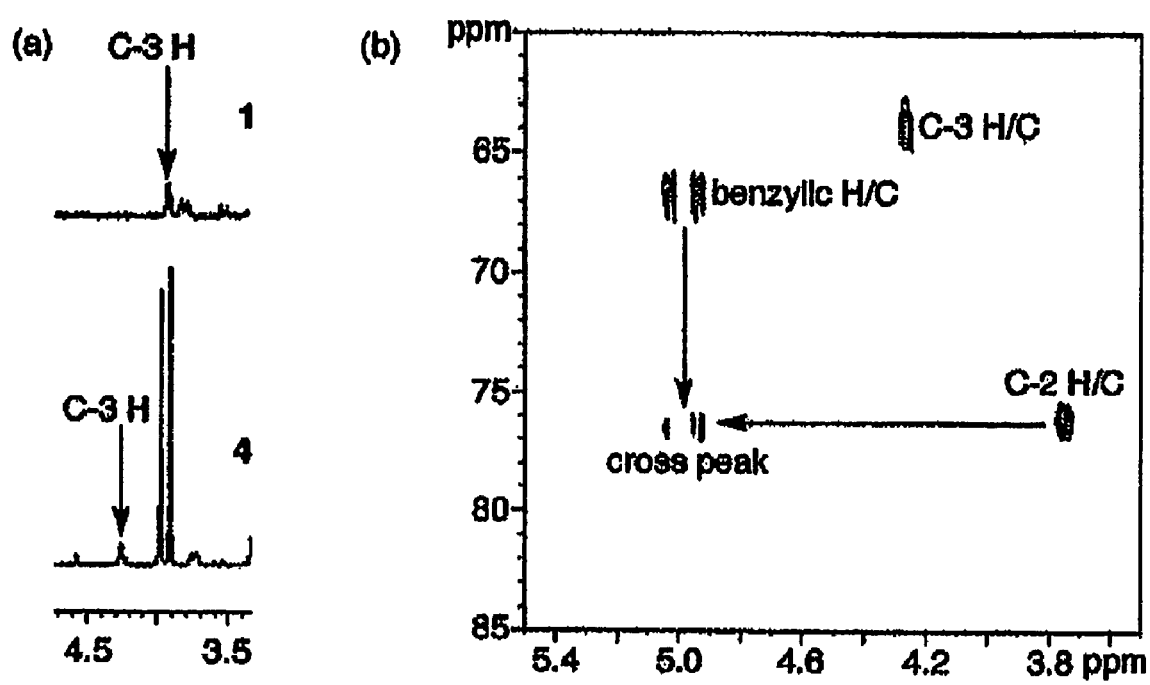
FIG. 3 is a line graph of experimental results showing the generation of luciferase activity as a function of time following photolysis. 293T cells that had been transiently transfected with plasmids encoding constitutively expressed EcR and RXR and inducibly expressed luciferase were exposed to caged β-ecdysone 4 for 16 hr and then either illuminated (♦) or first washed to remove extracellular 4 and then illuminated (▲). Control luciferase expression in the absence of ligand is shown as well (■). Percent maximal expression is normalized relative to the yield obtained for the 1 min photolysis time period.

The time-dependence of β-ecdysone-induced luciferase expression following photolysis is shown in FIG. 3. Cells were pre-incubated with the caged β-ecdysone 4 for 16 hr, illuminated for 1 min, and then lysed at various time points following photolysis. Maximal gene expression was observed at 16 hr. We also assessed whether 4 is cell permeable and undergoes intracellular uncaging upon photolysis. The 293T cell line was pre-incubated with 4 for 16 hr, the media subsequently removed, and the cells washed with PBS. Ecdysone-free media was then added, the cell culture incubated for various time points, and tested for luciferase activity. The gene expression kinetic profile is nearly identical for the two sets of experiments [(4+photolysis) versus (4+washing+photolysis)] during the first 5 hr, which is consistent with the notion that caged β-ecdysone 4 is intracellularly liberated (FIG. 3). However, we do note that (4+washing+photolysis) conditions achieve only 50% of the maximal activity displayed by β-ecdysone.

Figure 4:
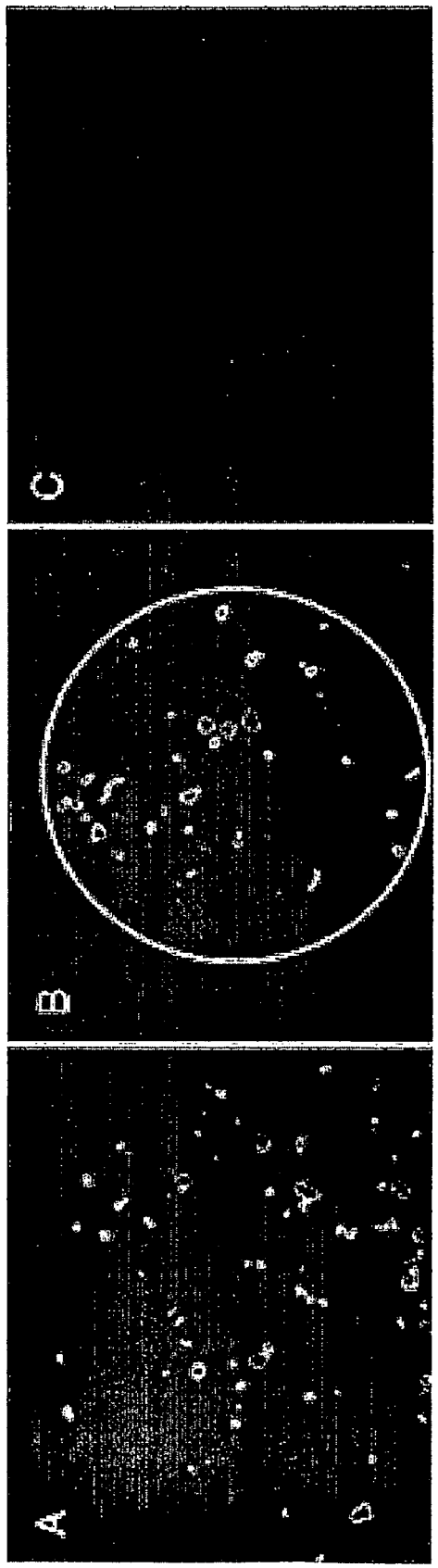
FIG. 4 shows micrographs of experimental results described in the Example. Panel (a) shows transfected 293T cells after exposure to β-ecdysone 1 and subsequent probing for luciferase expression. Panel (b) shows transfected 293T cells after exposure to 4, spot illumination (~0.25 mm$^2$) for 10 sec, and then probing for luciferase expression. Panel (c) shows the transfected 293T cells in the experiment as described in (b), outside of the region of illumination. The microscope used in these experiments was an Olympus IX-70 @10X, N.A. 0.3.

Light-Driven Spatially-Discrete Luciferase Expression in Transiently Transfected 293T Cells. We examined whether the combination of 4 and spot illumination induces gene activation in a spatially discrete fashion. Transiently transfected 293T cells were incubated with 1 for 16 hr, fixed, permeabilized, exposed to a luciferase antibody, and stained with an Alexa-labeled secondary antibody. As expected, luciferase expression (20% transfection efficiency) was observed throughout the general cell population (FIG. 4a). By contrast, cells incubated with the caged analog 4 under identical conditions failed to exhibit detectable luciferase expression (data not shown). 293T cells were also exposed to 4, the media replaced with fresh media to remove extracellular 4, and spot illuminated (~0.25 mm$^2$) for 10 sec. The cells were then returned to the incubator for 6 hr and subsequently analyzed for luciferase expression. Only those regions exposed to UV light display luciferase production (FIG. 4b/4c).

Discussion

The analysis of protein function in living animals has been and continues to be an exceedingly difficult endeavor. Even when function can be assigned to a specific protein, the phenotypic consequences of activation may not only be cell type specific, but can vary according to both when (e.g. embryo versus adult) and where (e.g. specific tissue microenvironments) activation/expression occurs. As a result, there is increasing interest in the development of methodologies to assess protein function in the whole organism with respect to both temporal and spatial parameters.

Inducible gene expression systems using transgenic animals allows one to examine the consequences of protein expression at any point during the lifetime of the animal. However, the issue of spatial control has only recently begun to be addressed. One strategy is the use of light to control where gene activation/protein expression transpires. Haselton and his colleagues reported the first example of light-driven gene expression in 1999 (Monroe et al., 1999). Those investigators prepared 1-(4,5-dimethoxyl-2-nitrophenyl)diazoethane multi-modified plasmids encoding either luciferase or green fluorescent protein. The latter were delivered via particle bombardment (rat skin) or liposome transfection (HeLa cells). Illumination of the transfected tissue/cells produced a 40-50% restoration of protein expression levels versus the control (i.e. transfection with uncaged plasmid). Recently, Okamoto and his colleagues prepared a coumarin caged mRNA encoding various proteins, including green fluorescent protein, β-galactosidase, and the transcription factor Engrailed2a, which were microinjected into Zebrafish embryos (Ando et al., 2001). An obvious advantage of the caged gene-based strategy is that it does not require the use of transgenic animals. Furthermore, it may ultimately be possible to simultaneously introduce and therefore switch on multiple genes. However, limitations include the need to resort to special delivery methods and that the mode of gene introduction renders protein expression transient. These characteristics suggest that the caged gene approach should prove ideal for the study of short-term biological phenomena in small cell populations (e.g. embryogenesis). Koh and his colleagues recently reported the preparation and use of a caged estradiol, which was used to activate the expression of an estrogen response element-controlled luciferase gene in transiently transfected HEK293 cells (Cruz et al., 2000). This strategy offers an exciting tool for examining the effect of hormones on endogenous gene expression profiles both in vitro and in vivo. Light-activatable, cell-permeable, small molecules possess the advantage of ready delivery throughout a large multicellular organism. In addition, in conjunction with the well-established Cre/loxP recombinase strategy (Ryding et al., 2001), a single treatment could potentially elicit permanent changes in gene expression patterns.

We describe herein the construction and analysis of a caged cell-permeable ecdysteroid. β-ecdysone and its structural congeners have no known effect on mammalian physiology. Consequently, only ecdysone response element-controlled transgenes should be activated upon photo-generation of the active ecdysteroid. We also demonstrate, for the first time, that a small caged cell-permeable molecule can be used to drive gene expression in a spatially-discrete fashion.

Maximal biological activity of ecdysteroids requires the presence of free hydroxyl groups at the C-2, C-3, and C-20 positions (see 1) (Dinan et al., 1999). Consequently, we sought to construct a chemically modified biologically inactive ecdysteroid via alkylation of one of these alcohol moieties. Subsequent light-based cleavage of the modifying agent from the alkylated ecdysone would then regenerate the native (and therefore biologically active form) of ecdysone.

A wide variety of structurally diverse caging agents have been described (Adams & Tsien, 1993). We chose the 4,5-dimethoxy-2-nitrobenzyl moiety for our initial studies because of its reasonably good photophysical properties ($\lambda_{max}$ and $\Phi$). Although a wide range of structurally modified ecdysteroids have been prepared during the last four decades, we are not aware of any example in which one (or more) of the hydroxyl groups on the β-ecdysone ring system has been alkylated. Indeed, our initial attempts to prepare 4,5-dimethoxy-2-nitrobenzylated β-ecdysone failed to generate any alkylated product. However, since the C-2/C-3-acetonide of β-ecdysone has been reported (Suksamrarm & Pattanaprateep, 1995), it occurred to us that it might be feasible to generate, in situ, the dibutylstannylene acetal 3. Stannylene acetals have been extensively employed in carbohydrate chemistry and these intermediates are known to undergo ready alkylation in a highly regioselective fashion (Grindley, 1998). For example, stannylene acetals of cis-diols in 6-membered rings tend to selectively undergo alkylation on the equatorial, rather than the axial, hydroxyl moiety. With these features in mind, we exposed 2 to the bromide 3 in the presence of CsF and obtained a monalkylated product (as assessed by mass spectrometry) in 90% yield. We subsequently employed a combination of DQF-COSY, HSQC, and HMBC NMR spectroscopies to demonstrate that monoalkylation of β-ecdysone occurs exclusively at the equatorial C-2 hydroxyl moiety to furnish 4.

Figure 5:
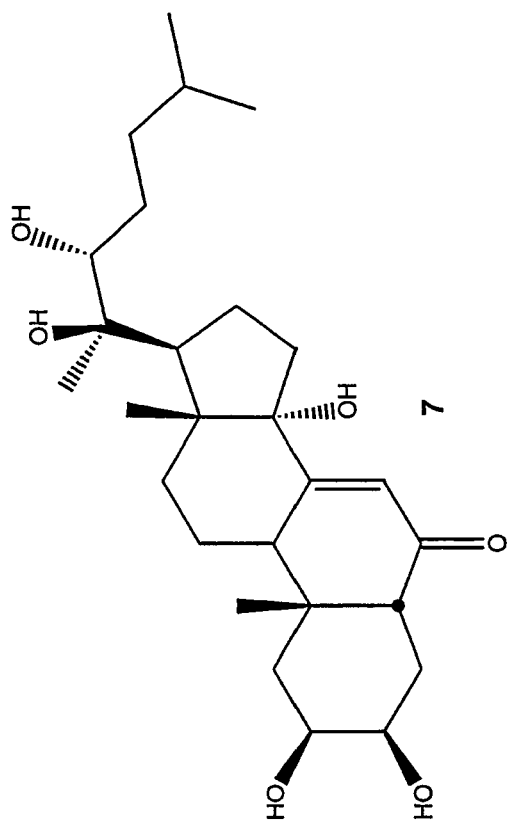
FIG. 5 shows the chemical structures of the β-ecdysone homologues muristerone 6 and ponasterone A 7.
Figure 5:
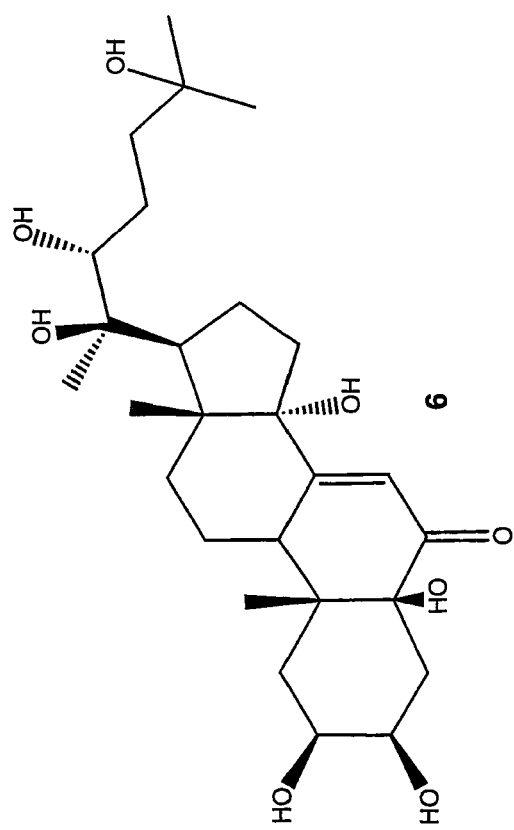

The ecdysone-inducible gene expression system was employed to assess the ability of β-ecdysone 1, and its caged counterpart 4, to induce luciferase expression in the absence and presence of light. We note that naturally occurring β-ecdysone homologues, such as muristerone 6 and ponasterone A 7 (FIG. 5), are 1,000-times as active as β-ecdysone and induce transcriptional activity of up to 20,000-fold in cell-based systems (No et al., 1996; Albanese et al., 2000). However, since these homologues are expensive, we chose to develop our initial chemistry on the more readily available congener 1. β-ecdysone induces a nearly 100-fold enhancement in luciferase activity versus background in 293T cells that were transiently transfected to constitutively express EcR/RXR and inducibly express luciferase (Table 1). By contrast, caged β-ecdysone 4 is virtually inactive. However, incubation of 293T cells with 4 and subsequent illumination for 1 min induces luciferase formation at a level that is nearly 60% of its native bioactive counterpart 1. The 60% restoration of luciferase activity is consistent with our observation that a 1 min photolysis time window converts approximately 60% of the caged compound 4 into the uncaged β-ecdysone as assessed by HPLC. Various control experiments confirmed that the caged derivative, in conjunction with light, is sufficient to activate the EcR/RXR expression system (see Results Section).

What is the time-dependence of β-ecdysone-induced luciferase expression? We addressed this question by pre-incubating 293T cells with the caged derivative 4 for 16 hr followed by illumination for 1 min. Cells were subsequently incubated for various time intervals, lysed, and luciferase activity assessed. Minimal luciferase activity was first observed at the 4 hr post-illumination time point and ultimately approached maximal activity levels at the 16 hr post-illumination time point (FIG. 3).

Is the caged derivative 4 cell permeable and does it undergo light-driven intracellular uncaging? In order to examine these issues, cells were once again incubated with 4 for 16 hr. However, the cell culture was subsequently washed with PBS to remove all extracellular 4. Ecdysone-free media was then added and the cells were immediately illuminated for 1 min. Under these conditions, the ecdysteroid should only be present in the intracellular compartment. The cells were then incubated for various time points, lysed, and the lysate subsequently tested for luciferase activity. Both sets of conditions (extracellular+intracellular caged β-ecdysone versus intracellular caged β-ecdysone only) furnish essentially identical kinetic profiles of luciferase induction over the first 6 hr following illumination. Thereafter, however, luciferase activity levels off and begins to decrease in the cell culture where caged β-ecdysone was removed from the extracellular milieu. The latter result may be due to the egress of intracellular β-ecdysone in the absence of an extracellular β-ecdysone concentration gradient.

These experiments suggest that 4 is both membrane permeable and intracellularly uncaged following photolysis. However, if photo-uncaged intracellular β-ecdysone does migrate to the extracellular environment then it is possible that sites distant from the region of illumination could undergo unintentional gene activation as well. On the other hand, given the small intracellular volume of a typical cell (~1 pL) it is likely that any uncaged β-ecdysone that escapes from its intracellular locale will be too dilute to effect changes in gene expression profiles at remote sites. We explicitly addressed this possibility by examining spatially-discrete gene activation using spot illumination of cultured 293T cells. Luciferase expression in fixed and permeabilized cells was visually identified via the coupled use of a luciferase antibody and a secondary Alexa-labeled antibody. Cells incubated with bioactive β-ecdysone 1 for 16 hr furnished global luciferase expression throughout the cell culture (FIG. 4a). Luciferase expression is not observed in the absence of β-ecdysone (data not shown) nor in the presence of caged β-ecdysone without light (see below). By contrast, spatially discrete luciferase expression is observed when 293T cells were incubated with caged β-ecdysone 4, subsequently washed to remove extracellular (but not intracellular) 4, spot illuminated (~0.25 mm$^2$) for 10 sec (FIG. 4b), and returned to the incubator for 6 hr. Regions outside of the zone of illumination fail to display luciferase expression. These results not only confirm that caged 4 and light are required to activate gene expression (FIG. 4c), but also indicate that a well-defined cellular zone of light-induced protein expression is feasible using this strategy.

Caged small molecules (e.g. ATP, NO, etc) have proven to be extraordinarily useful as reagents to help define temporal relationships in biochemical-mediated processes (Adams & Tsien, 1993). More recently, caged peptides and proteins have been described, and their use as tools to delineate the role of individual proteins in cell-based phenomena is underway (Curley & Lawrence, 1999; Marriott & Walker, 1999). Although concerns have been raised about the effect of light and/or the caging agent by-product on cell viability we, as well as others, have found that light-induced activation of caged compounds (from caged fluorophores to caged enzymes) has no obvious effect on cell viability. Indeed, cells behave as expected when the bioactive species is generated (see, e.g., the effect of caged cAMP-dependent protein kinase on cellular phenotype, as described by Curley & Lawrence, 1999). Some of these concerns arise as a consequence of the relatively long illumination times required for photoactivation in vitro, which are typically on the order of minutes. However, cell-based experiments performed under the microscope require only a few seconds to generate the uncaged species (due to a high photon flux through a narrow spatial window). In addition, although the nitrobenzyl byproduct of the uncaging process is an electrophile, extensive work with a wide variety of caged species has failed to uncover any apparent deleterious effects on cell performance or viability (possibly owing to the high intracellular concentration of glutathione, which may chemically add to and therefore neutralize the by-product) (Kaplan, 1978; Walker, 1988).

In summary, we have developed a light-initiated ecdysone-based gene activation strategy that furnishes both temporal and spatial control over protein expression in living cells. The ecdysone gene activation system is endowed with a number of favorable attributes, including low basal activity in the absence of, and high inducibility in the presence of, the ecdysteroid. Furthermore, ecdysteroids do not appear to have any effect on mammalian physiology. These characteristics, in conjunction with light-driven spatial control over where expression occurs, provide a means to assess the effect and influence of protein expression on phenotype as a function of tissue microenvironment. For example, tumorigenic potential is dependent, in part, on the ability of the tumor to overcome the unique growth suppressive influence associated with the distinctive microenvironment that harbors it (Roskelley & Bissell, 2002). In addition, tumor metastasis is known to be dependent upon the nature of the host microenvironment as well (Liotta & Kohn, 2001). Consequently, the ability to alter gene expression, in a microenvironment-specific fashion, should prove valuable in assessing the influence of protein function on the progression of both normal and disease-related phenomena.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference in their entireties. The discussion of the references herein is intended merely to summarize the assertions made by the authors and no admission is made that any reference constitutes prior art. Applicants reserve the right to challenge the accuracy and pertinence of the cited references.

What is claimed is:

1. A compound comprising a ecdysteroid ligand that specifically reacts with an ecdysone receptor and a molecular cage covalently bound to the ecdysteroid ligand that prevents reaction of the ecdysteroid ligand with the ecdysone receptor, wherein the ecdysteroid ligand is released from the cage and capable of reacting with the ecdysone receptor upon exposure of the compound to light and wherein the molecular cage comprises a nitromethoxybenzyl moiety.

2. The compound of claim 1, wherein the ligand is an inhibitor of the receptor.

3. The compound of claim 1, wherein the ligand is selected from the group consisting of ecdysone, 20-hydroxyecdysone, ponasterone A, muristerone A, and inokosterone.

4. The compound of claim 1, wherein the nitromethoxybenzyl moiety is 1-methyl-4,5-dimethoxy-2-nitrobenzene.

5. The compound of claim 4, wherein the compound is

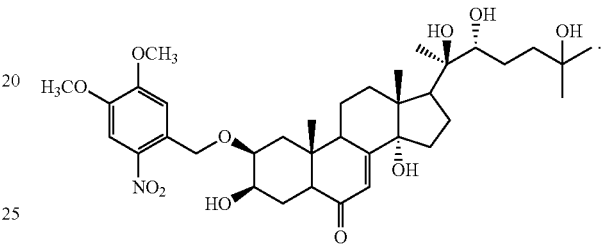

6. The compound of claim 1, wherein the molecular cage is a two-photon cage.

7. The compound of claim 1, wherein the light comprises wavelengths at 300-400 nm.

8. The compound of claim 1, wherein the light comprises wavelengths at 325-375 nm.

9. The compound of claim 4, wherein the compound is

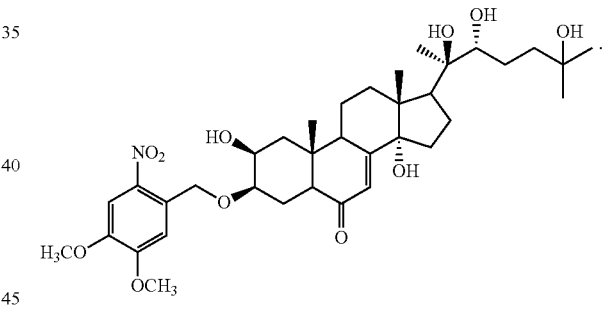

* * * * *

SEQUENCE LISTING

<160> NUMBER OF SEQ ID NOS: 1

<210> SEQ ID NO 1
<211> LENGTH: 34
<212> TYPE: DNA
<213> ORGANISM: Bacteriophage P1

<400> SEQUENCE: 1
ataacttcgt ataatgtatg ctatacgaag ttat                              34

UNITED STATES PATENT AND TRADEMARK OFFICE
CERTIFICATE OF CORRECTION

PATENT NO. : 8,076,318 B2
APPLICATION NO. : 10/532009
DATED : December 13, 2011
INVENTOR(S) : David S. Lawrence, Richard G. Pestell and Christopher Albanese Page 1 of 1

It is certified that error appears in the above-identified patent and that said Letters Patent is hereby corrected as shown below:

In the specification

Column 1, lines 10-16, should read:

-- STATEMENT OF GOVERNMENT SUPPORT

This invention was made with government support under grant numbers GM068993 and CA075503 awarded by the National Institutes of Health. The government has certain rights in the invention. --

Signed and Sealed this
Third Day of November, 2015

Michelle K. Lee
*Director of the United States Patent and Trademark Office*